United States Patent [19]

Murayama et al.

[11] 4,165,937
[45] Aug. 28, 1979

[54] MAGNETO-OPTIC SPECTROPHOTOMETER

[75] Inventors: Seiichi Murayama, Kokubunji; Masaru Ito, Kodaira; Manabu Yamamoto, Odawara; Kunifusa Kayama, Higashikanamachi; Kounosuke Oishi, Mito, all of Japan

[73] Assignee: Hitachi, Ltd., Japan

[21] Appl. No.: 746,831

[22] Filed: Dec. 2, 1976

[30] Foreign Application Priority Data

Dec. 5, 1975 [JP] Japan .................. 50-143979

[51] Int. Cl.² ........................................ G01J 3/42
[52] U.S. Cl. ................................ 356/319; 356/312
[58] Field of Search ..................... 356/88, 93–97, 356/85–87

[56] References Cited
U.S. PATENT DOCUMENTS 3,937,577  2/1976  Dorsch ........................ 356/96 X Primary Examiner—F. L. Evans
Attorney, Agent, or Firm—Craig and Antonelli

[57] ABSTRACT

A magneto-optic spectrophotometer for detection or identification of atoms or molecules contained in the sample by utilizing phenomena of birefringence or rotation of polarization caused by the atoms or the molecules in a magnetic field is constructed as follows. Linearly polarized lights are incident on a space where atoms or molecules to be detected exist in a magnetic field. The lights having passed through said space are separated into two beams of lights of polarization components perpendicular and parallel to the polarization of the incident lights. The perpendicular components are used as the signal lights, and the parallel components the reference lights. The signal lights and the reference lights are spectrally analyzed by a wavelength selector in which a signal light and a reference light of a wavelength to be selected are incident on an identical dispersive element. The signal lights and the reference lights are detected by respective detectors. Then, the ratios of the outputs of the signal light detectors to the outputs of the reference light detectors are obtained. By this construction the intensities of the scattered lights by atoms or molecules to be detected can precisely be measured.

12 Claims, 9 Drawing Figures

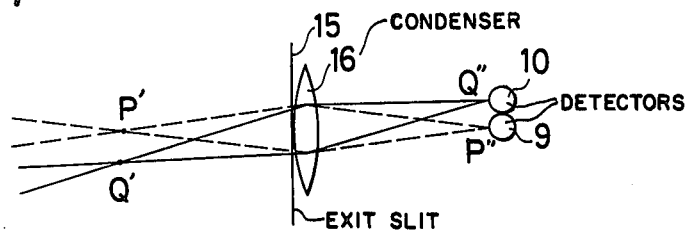
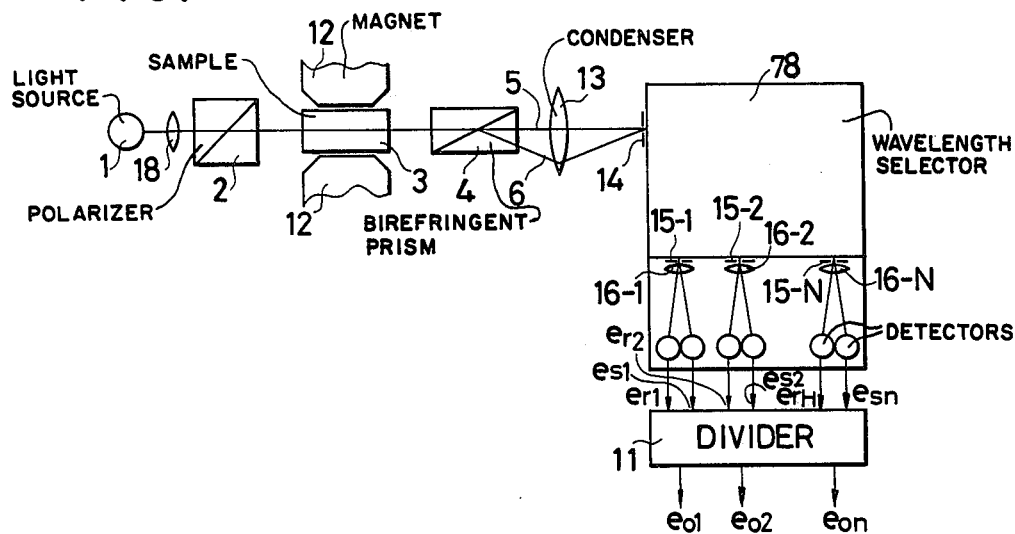
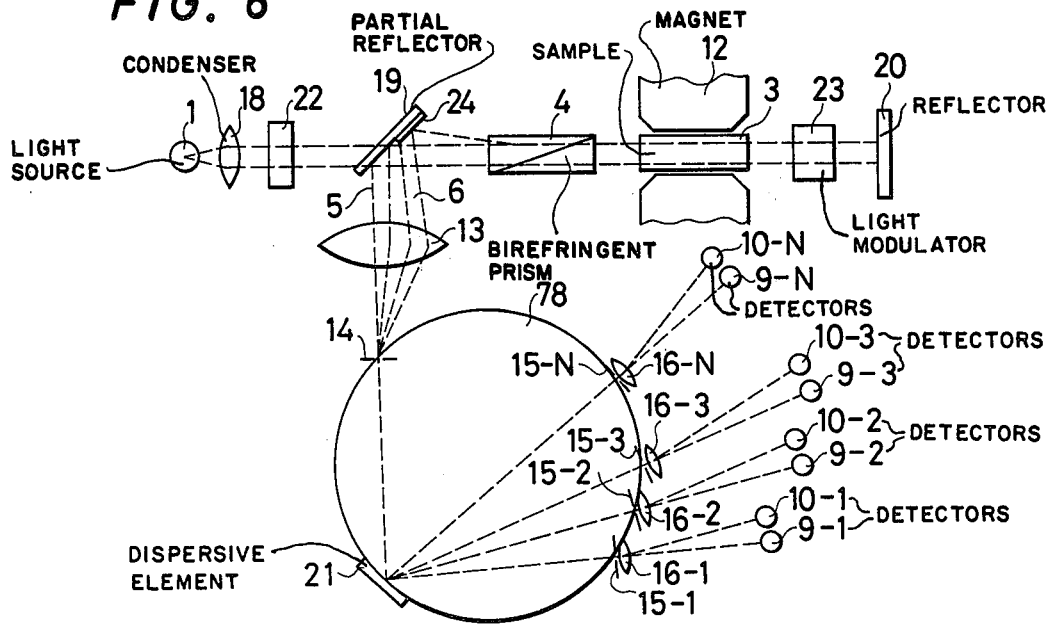

MAGNETO-OPTIC SPECTROPHOTOMETER

FIELD OF THE INVENTION

This invention relates to a spectrophotometer utilizing phenomena of birefringence or rotation of polarization caused by atoms or molecules in a magnetic field.

PRIOR ART OF THE INVENTION

Generally, as is well known, the intensity of light scattered by randomly positioned atoms or molecules is proportional to the square of the number of the scattering atoms or molecules, if the scattering is the Rayleigh scattering or the resonance scattering, where the wavelength of the scattered light is equal to that of the incident light, and if the direction of propagation of the scattered light is identical with that of the incident light (the forward scattering). The intensity of light scattered to any other direction is linearly proportional to the number of the scattering atoms or molecules.

In case of the resonance scattering where the wavelength of the incident light agrees with that of the resonance line of atoms or molecules, the intensity of the scattered light is much higher than in case of non-resonance scattering. The wavelengths of the resonance lines are different in each kind of atoms and molecules, and the resonance lines are narrow in wavelength width. Accordingly, it is possible to identify atoms and molecules by wavelengths of scattered lights, and to measure the numbers of the atoms and the molecules by the intensities of the scattered lights.

Comparing with absorption and fluorescence, scattering is a process of higher order, and the scattering cross section of an atom or a molecule is smaller. However, if the scattered light is observed from the forward direction, it is easily detected even when the number of scattering atoms or molecules is small, because the intensity of the forward scattered light is proportional to the square of the number of scattering atoms or molecules, and the total cross section is large. In this case, it is necessary to provide a means to separate the scattered light from the incident light, because there is no difference in wavelength and propagation direction between the scattered light and the incident light. In order to separate the scattered light and the incident light, the magneto-optic effects, namely the Faraday effect (rotation of polarization) and the Voigt effect (birefringence), caused by atoms or molecules in a magnetic field may be utilized. In this case, the scattered light and the incident light are separated by difference in polarization.

Hereinafter, a conventional method to separate the scattered light and the incident light will be described. A light radiated from a light source, which has a spectral distribution including the resonance line of atoms or molecules to be measured, is turned into a linearly polarized light by the first polarizor, and said linearly polarized light is incident on a space where atoms or molecules to be measured exists. A magnetic field parallel or perpendicular to the optical path is externally applied to said space. Arrangements with magnetic fields parallel and perpendicular to the optical path are hereafter called the Faraday and the Voigt arrangements, respectively. In the Voigt arrangement, a magnetic field is applied to the direction with an angle of 45° to the polarization of the first polarizor.

The forward scattered lights have different polarization components from the incident light having passed through the first polarizor due to the Faraday effect or the Voigt effect. A part of these components passes through the second polarizor (the analyser) whose polarization is perpendicular to that of the first polarizor, and is detected by a photodetector as a signal.

In this method, it is desirable that elements to be detected are in said space in the state of an atom. Generally, most of elements are contained in the sample in the state of molecules formed by combinations with other elements. In order to dissociate these molecules, it is necessary to supply energy to the sample, and to break the molecular bonds. Conventionally, the sample is introduced into a flame or an oven at high temperature, and is subjected to thermal dissociation. In the high temperature flame or oven, other kinds of molecules are produced as well as the dissociated atoms. These molecules may absorb the incident light, and the intensity of the light which can magneto-optically interact on atoms or molecules to be detected may decrease by the absorption. This makes the intensity of the forward scattered light decrease. Small particles like smoke may scatter the incident light, and also decrease the intensity of the forward scattered light. In the method above mentioned which does not have any compensating means against these absorption by molecules and scattering by small particles, errors in the measurement are large.

The inventors of the present application filed a photometer with a means which automatically eliminates the above mentioned defect as a Japanese patent of the application No. 15330/75 entitled "Photometer utilyzing magneto-optic effects." In the invention of the patent application No. 15330/75, a birefringent prism is used as the second polarizor (analyser), which is enable to split the incident light into two light beams of polarizations perpendicular each other. The light beams of polarizations perpendicular and parallel to the polarization of the first polarizor are used as the signal light and the reference light, respectively. The decrease in the intensity of the forward scattered light due to the absorption by molecules and the scattering by small particles is compensated by obtaining the ratio of the intensity of the signal light to the intensity of the reference light.

According to the theory of A. Corney et al. described in "Proceedings of the Royal Society of London" Vol. A293, p. 70 (1966), the intensity of the signal light is calculated to be nearly $1/10^4$ times as large as the intensity of the incident light, if the element to be detected is mercury, if the space where the incident light magneto-optically interacts on mercury atoms is 10 cm long, if the pressure of the space is one atmosphere, if a magnetic field of about 5 k Oe is applied to the space parallel to the optical path (the Faraday arrangement), and if the incident light has a spectral distribution of 20 Å in width including the wavelength of the resonance line of mercury. This result of calculation indicates that the intensity of the signal light is weak, and that the energy of the incident light is converted into the energy of the signal light by a very small amount. Accordingly, the intensity of the reference light is nearly equal to the intensity of the incident light which magneto-optically interacts on atoms or molecules to be detected. Therefore, the ratio of the intensity of the signal light to the intensity of the reference light is independent of processes of absorption by molecules and scattering by small particles. Consequently, the number of atoms or molecules to be detected can precisely be measured. Although this method is a kind of modification of the so-called two wavelength method, it is completely different from the two wavelength method in the following points. The signal light and the reference light have the same wavelength, and are radiated from the same light source. Only in polarization they are different from each other. Therefore, more precise measurements can be made than in the two-wavelength method.

In the method described in the patent of the application No. 15330/75, the signal light and the reference light are directly detected by the respective photodetectors without using wavelength selectors. In this method lights of different wavelengths from the resonance wavelength may be included in the signal light and the reference light. Especially the reference light may contain almost entire spectrum of the light source. This makes it difficult to measure accurately the number of atoms or molecules to be detected.

To eliminate this disadvantage, a magneto-optic spectrophotometer shown in FIG. 1 has a wavelength selector between the birefringent prism and the photodetectors. Lights radiated from a light source which has a spectral distribution including the resonance wavelengths of atoms or molecules to be detected are turned into linearly polarized lights by a polarizor 2 whose polarization is shown by an arrow $P_1$ in FIG. 1. Said linearly polarized lights are incident on a space 3 in which the sample containing atoms or molecules to be detected exists. Generally, the inner space of a sample heating furnace made of material of high melting point such as graphite, tantalum or the like is often used as said space 3. A magnetic field is externally applied to said space 3 to the direction of an arrow $H_P$ (parallel to the optical path) or an arrow $H_V$ (perpendicular to the optical path) shown in FIG. 1. Atoms or molecules in said space 3 to be detected forward scatter lights of their resonance wavelength incident on said space 3. The forward scattered lights have a polarization component $P_2$ perpendicular to $P_1$ due to the Faraday effect or the Voigt effect. Lights having passed through said space 3 are separated into the light of polarization $P_2$ (signal light) and the light of polarization of $P_1$ (reference light) when passing through a birefringent prism 4. If the signal light travels along an optical path 5, the reference light does along an optical path 6. Then, they are incident on wavelength selectors 7 and 8, respectively. The signal light and the reference light of the resonance wavelength of atoms or molecules to be detected are selected by said wavelength selectors 7 an 8, and are detected by photodetectors 9 and 10, respectively. The output $e_s$ of the photodetector 9 is proportional to the intensity of the forward scattered light, while the output $e_r$ of the photodetector 10 is proportional to the intensity of the incident light which magneto-optically interacts on atoms or molecules to be detected, since the intensity of the forward scattered light is small. The output $e_s$ is divided by the output $e_r$ in a divider 11. As described previously, the output $e_o$ of the divider 11 is independent of the absorption by other molecules and the scattering by small particles.

The above method has difficulties as follows. Two wavelength selectors are required, and the construction is complicated. Accordingly, the photometer is expensive, and not easy in handling.

SUMMARY OF THE INVENTION

This invention has for its object to eliminate the above-mentioned disadvantages of the prior-art method and to thereby provide a magneto-optic spectrophotometer which is small in size, low in cost and easy in handling.

In order to accomplish the object, the spectrophotometer of this invention is so constructed that signal light and reference light which are separated by a polarization prism are condensed by a condenser, that both the lights are brought into incidence on an identical wavelength selector and spectrally analyzed therein, and that the respective lights are thereafter detected by individual photodetectors (a signal light detector and a reference light detector).

Hereunder, the embodiments of this invention will be described with reference to the drawing.

BRIEF DESCRIPTION OF THE DRAWINGS

FIG. 3 and FIG. 4 are fragmentary, detailed, illustrative views of the optical path shown in FIG. 2.

FIG. 5, FIG. 6 and FIG. 7 are illustrative views of the other embodiments of the present invention.

DESCRIPTION OF THE PREFERRED EMBODIMENTS

Embodiment 1

Figure 1:
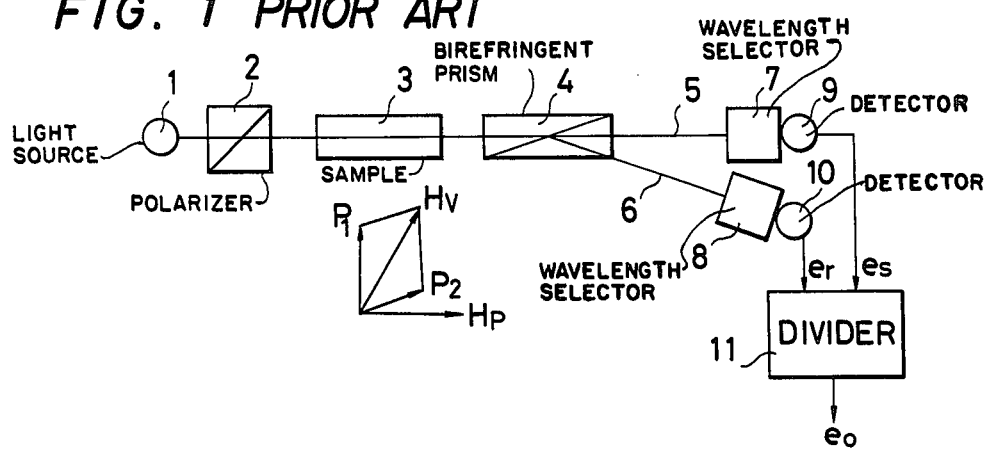
FIG. 1 is an illustrative view of the embodiment of the prior art.
Figure 2:
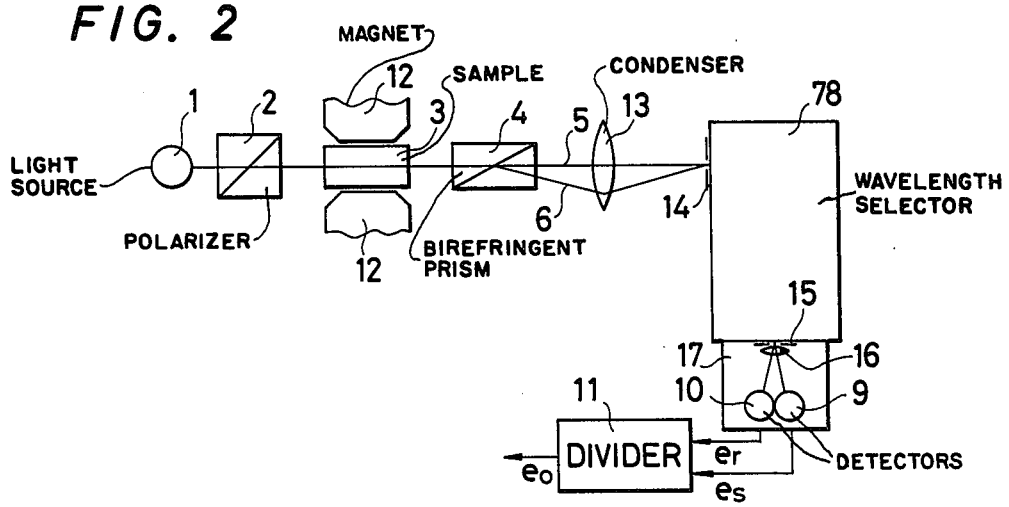
FIG. 2 is an illustrative view of one embodiment of the present invention.

FIG. 2 is a diagram showing an embodiment of this invention. In the figure, numeral 1 designates a light source, numeral 2 a polarizer, numeral 3 a space in which a sample containing atoms to-be-detected exists, numeral 4 a polarization prism, numeral 5 an optical path of signal light, numeral 6 an optical path of reference light, numerals 9 and 10 photodetectors, numeral 11 a divider, numeral 12 magnetic poles for applying a magnetic field to the space 3, numeral 13 a condenser, numeral 78 a wavelength selector, numeral 14 an entrance slit of the wavelength selector 78, numeral 15 an exit slit of the wavelength selector 78, numeral 16 a condenser, and numeral 17 a camera for setting the photodetectors 9 and 10 therein.

Employed as the polarization prism 4 is a birefringent crystal plate made of calcite, quartz or the like, or a birefringent prism with which optical paths of ordinary rays and extraordinary rays are separated, for example, Senarmont prism, Glan Thompson prism, Glan Taylor prism, Rochon prism or Wollaston prism. Hereinafter, the polarization prism shall be called the birefringent polarizer.

The light source 1 is an incoherent light source which radiates the natural light. The light emergent from the light source 1 is turned by the polarizer 2 into linearly polarized light, which comes into incidence on the space 3. The magnetic field is externally applied to the space 3 by the magnetic poles 12. Owing to the magneto-optic effect, the light incident on the space 3 generates the signal light (forward scattered light) which has a polarization component orthogonal to the incident light. The light having passed through the space 3 is separated into the signal light and the reference light when passing through the birefringent polarizer (polarization prism) 4. In FIG. 2, the birefringent polarizer 4 is arranged so that the signal light may travel along the optical path 5 and that the reference light may travel along the optical path 6. The signal light and the reference light are condensed on the position of the entrance slit 14 of the wavelength selector 78 by the condenser 13, and they are brought into incidence on the wavelength selector 78. The signal light and the reference light are spectrally analyzed by the identical wavelength selector. In other words, the signal light and the reference light are subjected to the wavelength selection by means of an identical dispersive element installed within the wavelength selector. When the wavelength of the resonance line of the sample atoms is selected by the wavelength selector 78, the signal light having the wavelength of the resonance line and the reference light emerge into the camera 17 from the exit slit 15. The signal light and the reference light emergent from the exit slit 15 separate again, and are condensed on individual positions by the condenser 16. Then, they are detected by the photodetectors 9 and 10. When a signal light output $e_s$ of the photodetector 9 is divided by a reference light output $e_r$ of the photodetector 10 by means of the divider 11, an output $e_o$ is obtained.

Figure 3:
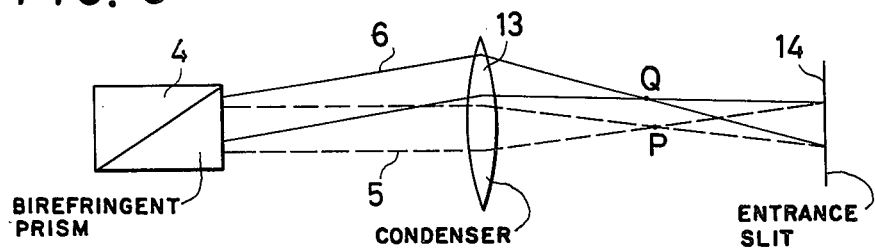

FIGS. 3 and 4 show the details of the optical paths of the signal light and the reference light.

Referring to FIG. 3, the signal light 5 and the reference light 6 separated by the birefringent polarizer 4 are substantially close to collimated beams. After passing through the condenser 13, therefore, they are once condensed on two points P and Q on a focal plane of the condenser 13, respectively. When, at this time, the entrance slit 14 of the wavelength selector is arranged at a position at which the image of the section of the central part of the birefringent polarizer 4 is formed by the condenser 13, the signal light and the reference light can be condensed on an identical position of the entrance slit 14. Accordingly, both the signal light and the reference light can be brought into incidence on the wavelength selector from the entrance slit 14. In this case, it is preferable that the angle of view of the two points P and Q from the entrance slit 14 is smaller than the angle of view of the dispersive element of the wavelength selector from the entrance slit 14.

In general, the wavelength selector has the optical property that the image of the entrance slit 14 appears at the position of the exit slit 15 for the light of the selected wavelength. For this reason, the signal light and the reference light incident from the entrance slit 14 emerge from the exit slit 15. As shown in FIG. 4, the images of the two points P and Q in FIG. 3 appear at the positions of two points P' and Q' on this side of the exit slit 15. Accordingly, the signal light and the reference light separate again after passing through the exit slit 15. In FIG. 4, the images P" and Q" of the respective points P' and Q' are formed by the condenser 16, and the photodetectors 9 and 10 are arranged at the positions of the respective points P" and Q" so as to individually detect the signal light and the reference light.

When, as the condenser 16, one having a focal length at which the points P' and Q' come to lie on the focal plane thereof is selected, the signal light and the reference light become two collimated beams of different traveling directions after passing through the condenser 16. It is also possible to detect the signal light and the reference light by the photodetectors 9 and 10 at positions at which the two collimated beams have separated. It is yet also possible to condense the two collimated beams by a further condenser and to thereafter detect the signal light and the reference light by the photodetectors 9 and 10.

Embodiment 2

FIG. 5 is a diagram showing another embodiment of this invention. In this embodiment, in order to raise the parallelism of the light beam emergent from the light source, a condenser 18 is arranged between the light source 1 and the polarizer 2. Further, in order to make it possible to measure forward scattered lights based on many kinds of elements at the same time, exit slits 15-1, 15-2, ... and 15-N are provided at those positions of the wavelength selector 78 at which the images of the entrance slit 14 are formed by lights of the wavelengths of the resonance lines of the respective elements, and simultaneously therewith, N sets of condensers 16-1, 16-2, ... and 16-N and photodetectors 9-1, 9-2, ... and 9-N as well as 10-1, 10-2, ... and 10-N which correspond to the exit slits are provided. By dividing each signal light output $e_{si}$ by the corresponding reference light output $e_{ri}$, an output $e_{oi}$ for the forward scattered light of the i-th element is obtained. In the apparatus for simultaneously analyzing many elements as in the present embodiment, the signal light and the reference light relevant to one of the many elements are subjected to the wavelength selection by an identical dispersive element.

Embodiment 3

FIG. 6 is a diagram showing still another embodiment of this invention. The light from the light source 1 is made a collimated beam by the condenser 18. After it passes through a reflector 19 having a light transmitting part, it comes into incidence on the birefringent polarizer 4. In passing through the birefringent polarizer 4, the incident light is separated into ordinary rays and extraordinary rays. For example, the ordinary rays propagate rectilinearly to come into incidence on the space 3, and they are reflected by a reflector 20 to retrograde along the identical optical path again. The extraordinary rays whose traveling path has been deflected by the birefringent polarizer 4 do not come into incidence on the space 3.

Owing to the presence of the reflector 20, also the forward scattered light generated in the space 3 by the magneto-optic effect, i.e., the signal light comes eventually into incidence on the birefringent polarizer 4 again. Since the signal light differs from the incident light in the polarization direction, its traveling path is deflected by the birefringent polarizer 4. The deflected signal light is reflected by a mirror surface part 24 of the reflector 19, and is condensed on the position of the entrance slit 14 of the wavelength selector 78 by the condenser 13. The condensed light comes into incidence on the wavelength selector 78 from the entrance slit 14, and is spectrally analyzed by a dispersive element 21. Now, in case of detecting the forward scattered lights of N elements at the same time, exit slits 15-1, 15-2, ... and 15-N are provided at positions on which the resonance lines of the respective elements are condensed, and the light intensities of the respective resonance lines are detected by photodetectors 9-1, 9-2, ... and 9-N.

On the other hand, the ordinary rays which have come into incidence on the space 3 are partially taken out as reference light by the light transmitting part of the reflector 19. This reference light is also condensed on the position of the entrance slit 14 of the wavelength selector 78 under the action of the condenser 13 so as to come into incidence on the wavelength selector 78. The reference light is spectrally analyzed by the dispersive element 21 likewise to the signal light, and the referene light intensities of the respective resonance lines are detected by photodetectors 10-1, 10-2, . . . and 10-N different from those for the signal lights. An output of the photodetector 9-i is divided by an output of the photodetector 10-i. Thus, an accurate measurement of the forward scattered light based on the i-th element can be carried out, as the decrease in the intensity of the light magneto-optically interacting on atoms due to the scattering by small particles and the absorption by molecules is compensated by the division. Although electronic circuitry is omitted from the illustration of FIG. 6, it may be the same as in FIG. 5. In case of the construction of the reflection type as in the present embodiment, the condenser 13 may be omitted in such a way that the reflector 19 is also endowed with the light condensing function by making it a concave mirror such as parabolic mirror, elliptic mirror and spherical mirror.

In the above, the light source 1 is intermittently lit up at a frequency $f_1$, or the light incident on the space 3 is modulated at the frequency $f_1$ by a light modulator, such as light chopper, 22. Further, the reflector 20 is subjected to rotational vibrations or a light modulator 23 is put in the optical path between the birefringent polarizer 4 and the reflector 20, thereby to modulate the signal light and the reference light at a frequency $f_2$. By way of example, a condition of $f_1 > > f_2$ is set. Under this condition, the outputs of the photodetectors 9 and 10 are selectively amplified at the frequency $f_1$ and detected, whereupon they are further selectively amplified at the frequency $f_2$ and detected. Then, the signal light and the reference light are obtained at high S/N (signal-to-noise) ratio. That is, the ambient light undergoes no modulation, light reflected from the birefringent polarizer 4 and scattering light of the light incident on the reflector 19 are modulated by only the frequency $f_1$, and the light emitted from the space 3 is modulated by only the frequency $f_2$. Accordingly, these lights can be removed from the signal light and the reference light, and the measurement at extraordinarily high S/N ratio becomes possible.

Embodiment 4

Figure 7:
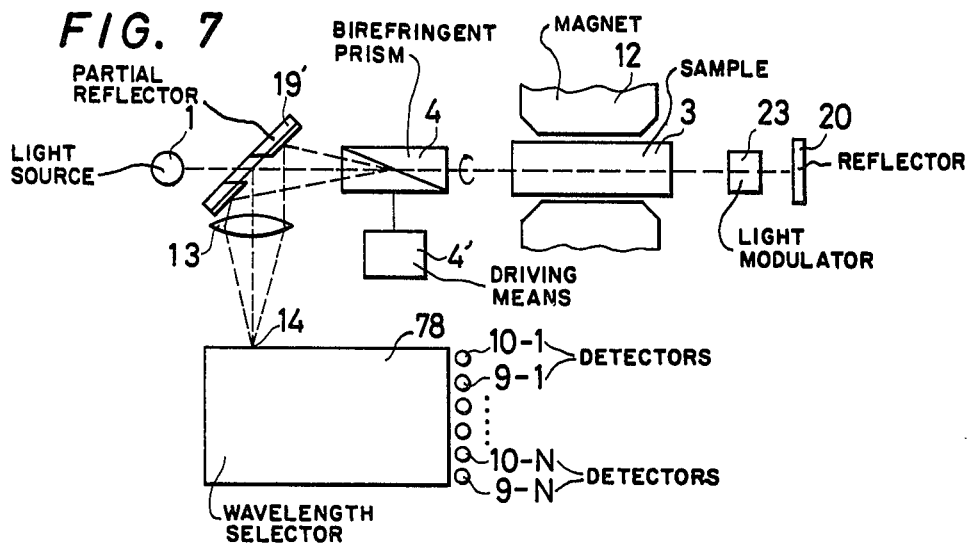

The foregoing embodiments have exemplified the case where the signal light and the reference light come to the same points at the positions of the entrance slit and the exit slit of the wavelength selector. FIG. 7 illustrates a case where the signal light and the reference light are condensed on two different places of the entrance slit of the wavelength selector and where the signal light and the reference light separated at the position of the exit slit are detected by individual photodetectors. Although this embodiment is the same in outline as the embodiment of FIG. 6, a reflector 19' is different from the reflector 19 in FIG. 6 as will be described later. Another point of difference from the embodiment of FIG. 6 is that the condensers 16-i on the exit slit side are omitted and that the photodetectors 9-i and 10-i are provided at the position of the exit slit of the wavelength selector 78. Further, driving means 4' for rotating the birefringent prism 4 at a frequency $f_3$ about the optical axis is added. In general, in case of applying a magnetic field in a direction perpendicular to an optical path, the intensity of signal light becomes the maximum when the polarization direction of incident light inclines by an angle of 45° to the direction of the magnetic field, and it becomes zero when the polarization direction is perpendicular or parallel to the magnetic field. By rotating the birefringent polarizer 4, accordingly, the signal light incident on the wavelength selector 78 is modulated by a frequency $4 f_3$. Therefore, the frequencies $f_2$ and $f_3$ are determined so as to satisfy $f_2 > > 4 f_3$ in advance, and after the outputs of the photodetectors 9 and 10 are selectively amplified at the frequency $f_2$ and once detected, the detected outputs are selectively amplified at the frequency $4 f_3$. Then, the signal light and the reference light can be separated from stray light, ambient light, light produced in the space 3, etc., and the S/N ratio can be sharply improved.

Figure 8:
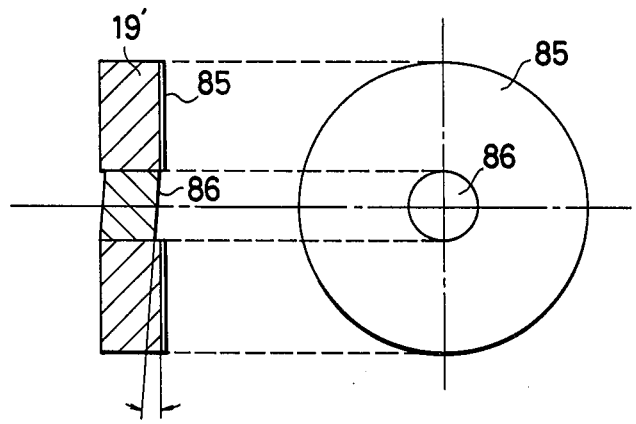
FIG. 8 is a detailed, illustrative view of the reflector shown in FIG. 7.

Means for condensing the signal light and the reference light onto the different positions on the opening of the entrance slit 14 will now be described more in detail. In this case, the word "slit" shall cover two pinholes provided at different positions. FIG. 8 shows a front view and a sectional view of the reflector 19'. The section taken is a plane containing the optical path and being substantially perpendicular to the paper as viewed in FIG. 7. Numeral 85 designates a reflective surface for the signal light, which is formed by, for example, evaporating aluminum onto the surface of the reflector. Numeral 86 indicates a reflective surface for the reference light, which is light-permeable and which inclines by a predetermined small angle $\theta$ with respect to the reflective surface 85.

Figure 9:
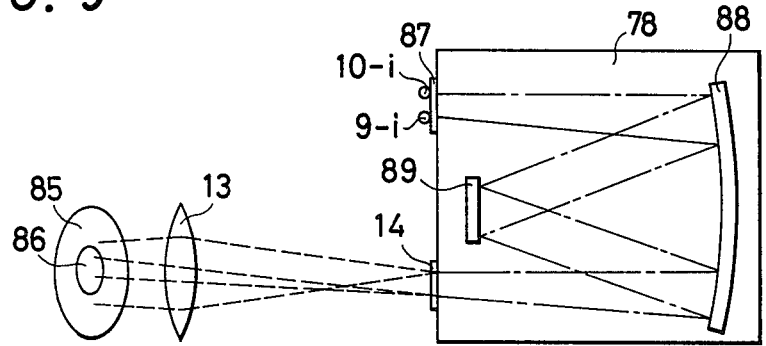
FIG. 9 is a illustrative view of the optical path of the signal light and the reference light in the embodiment shown in FIG. 7.

FIG. 9 shows the traveling paths of the signal light and the reference light after being reflected by the reflector 19'. Since, as previously stated, the reflective surfaces 85 and 86 of the reflector 19' incline by the small angle $\theta$, the two light beams are condensed on different positions under the action of the condenser 13. Since a straight line at which the reflective surfaces 85 and 86 intersect is parallel to the paper of FIG. 7 (perpendicular to the paper of FIG. 9), the signal light and the reference light can be condensed on the opening of the entrance slit 14 of the wavelength selector 78 as is provided in a direction perpendicular to the paper of FIG. 7 (parallel to the paper of FIG. 9). When, as the wavelength selector 78, there is employed one having an optical system capable of forming the image of the entrance slit at the position of the exit slit 87, the signal light and the reference light are again condensed on different positions at the exit slit 87. They are detected by the individual photodetectors 9-i and 10-i. In the case of FIg. 9, the wavelength selector employed is one of the type mounting. The lights incident from the entrance slit 14 are made collimated beams by a concave mirror 88, and come into incidence on a plane diffraction grating 89. The lights are dispersed by the plane diffraction grating 89 functioning as a dispersive element, and are again condensed on the different positions of the exit slit 87 by the concave mirror 88.

The embodiment thus far described is a modification of the reflection type apparatus shown in FIg. 6. Of course, the concept of the present embodiment is also applicable to the transmission type. By way of example, in the apparatus of FIG. 2, the entrance slit may be located at the points P and Q indicated in FIG. 3.

The reason why the signal light and the reference light are received by the individual photodetectors in the above embodiments is as described below. In case of detecting a very small amount of atoms, the forward scattered light being the signal light is often very weak in comparison with the reference light as has previously been stated. For example, the intensity ratio between the signal light and the reference light can become $10^{-3}$ or so. If, in such case, the signal light and the reference light are received by an identical detector in synchronism with the chopper means installed on the optical path, the S/N ratio will become inferior.

While the preferred embodiments of this invention have been described above in detail, they are only parts of this invention, and several modifications can be easily conjectured. By way of example, several modifications of the optical system are possible in dependence on the mounting of the wavelength selector. In case where the values of the light intensities of the signal light and the reference light have a large difference, a grey filter or a stop can be inserted in a suitable place of the optical path.

What we claim is:

1. In a magneto-optic spectrophotometer comprising means for irradiating sample materal by linearly polarized light of multiple wavelengths, means for applying a magnetic field to said sample material, polarizing means utilizing birefringence for separating light having passed through said sample material into signal light and reference light, means for selecting at least one wavelength for each of said signal light and said reference light, and means for detecting the signal light and the reference light at the wavelength selected by said wavelength selecting means, the improvement comprising light condensing means for bringing the signal light and the reference light into incidence on the same dispersive element of said wavelength selecting means to select a given wavelength for said signal light and said reference light, and means for enabling said signal light and said reference light at said selected wavelength to be detected by respective detectors of said light detecting means, wherein said signal light and reference light are provided by a light source with a continuous spectral distribution having resonance wavelengths of atoms and molecules to be detected.

2. A magneto-optic spectrophotometer according to claim 1, wherein means are provided for obtaining the ratio of the output of the signal light detector to the output of the reference light detector.

3. A magneto-optic spectrophotometer according to claim 1, wherein respective pairs of detectors are provided of said light detecting means for signal and reference lights at resonance wavelengths of a plurality of elements, and wherein means are provided for obtaining respective ratios of the outputs of the signal light detectors to the outputs of the reference light detectors for each element.

4. A magneto-optic spectrophotometer according to claim 1, wherein said light condensing means is so arranged to condense said signal light and said reference light on an identical position of an entrance of said wavelength selecting means, and further light condensing means separate said signal light and said reference light emerging from identical positions of exits of said wavelength selecting means.

5. A magneto-optic spectrophotometer comprising:
    means for providing a source of light;
    first light reflecting means having a semi-transparent portion for transmitting light from said source, said first light reflecting means having a reflecting portion;
    polarizing means utilizing birefringence for polarizing light transmitted by said semi-transparent portion;
    a sample material being irradiated by polarized light from said birefringence polarizing means;
    means for applying a magnetic field to said sample material;
    second light reflecting means for reflecting light passing through said sample material to retrograde back through said sample material and be incident on said birefringence polarizing means;
    said birefringence polarizing means separating said retrograde light from said sample material into signal light and reference light;
    said signal light and said reference light being respectively reflected by said reflecting portion and said semi-transparent portion of said first light reflecting means;
    means for selecting at least one wavelength for each of said signal light and said reference light which have been reflected by said first reflecting means, said wavelength selecting means including a dispersive element for selecting a given wavelength of both said signal light and said reference light; and
    means for detecting said signal light and reference light at said given selected wavelengths by said dispersive element, said detecting means including respective detectors for each of said signal light and reference light at each selected wavelength.

6. A magneto-optic spectrophotometer according to claim 5, wherein said sample material contains plural elements, said detecting means including respective pairs of said respective detectors for signal and reference light of resonance wavelengths of said plural elements, and wherein means are provided for obtaining respective ratios between outputs of said detectors for said signal light and outputs of said detectors for said reference light.

7. A magneto-optic spectrophotometer according to claim 5, wherein said reflecting portion and said semi-transparent portion of said first reflecting means have surfaces at a small angle inclination to each other so that said signal light and said reference light enter said wavelength selecting means at different positions.

8. A magneto-optic spectrophotometer according to claim 5, wherein light condensing means are provided between said first reflecting means and said wavelength selecting means for directing said signal light and said reference light to an entrance slit of said wavelength selecting means.

9. A magneto-optic spectrophotometer according to claim 5, wherein a light modulator is provided between said light source means and said first light reflecting means.

10. A magneto-optic spectrophotometer according to claim 5, wherein a light modulator is provided between said sample material and said second light reflecting means to modulate said signal light and said reference light.

11. A magneto-optic spectrophotometer according to claim 5, wherein said second light reflecting means is subject to rotation to modulate said signal light and said reference light.

12. A magneto-optic spectrophotometer according to claim 5, wherein means are provided for rotating said birefringence polarizing means about the optical axis.

* * * * *